United States Patent
Zhou et al.

(10) Patent No.: US 9,522,870 B2
(45) Date of Patent: Dec. 20, 2016

(54) 2,5-DISUBSTITUTED-1,4-DIAMINOBENZENES

(75) Inventors: Zhang-Lin Zhou, Palo Alto, CA (US);
Si-Ty Lam, Pleasanton, CA (US);
Lihua Zhao, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 258 days.

(21) Appl. No.: 13/416,904

(22) Filed: Mar. 9, 2012

(65) Prior Publication Data

US 2013/0237725 A1 Sep. 12, 2013

(51) Int. Cl.
*C07C 211/00* (2006.01)
*C07C 211/50* (2006.01)
*C09B 51/00* (2006.01)
*G11B 7/246* (2013.01)

(52) U.S. Cl.
CPC ............ *C07C 211/50* (2013.01); *C09B 51/00* (2013.01); *G11B 7/246* (2013.01)

(58) Field of Classification Search
CPC ............................ C07C 209/68; C07C 221/00
See application file for complete search history.

(56) References Cited

U.S. PATENT DOCUMENTS

| | | | | |
|---|---|---|---|---|
| 4,110,113 A | * | 8/1978 | Melzer et al. | 430/223 |
| 4,177,195 A | * | 12/1979 | Bingham | 549/280 |
| 2012/0088040 A1 | * | 4/2012 | Matsumori et al. | 428/1.26 |

FOREIGN PATENT DOCUMENTS

JP 201142607 * 3/2011 ........... C07C 211/53

OTHER PUBLICATIONS

JP-201142607 machine translation (2011).*
Ito et al. in Cancer Science 94(1), 3-8 (2003).*

* cited by examiner

*Primary Examiner* — Clinton Brooks
(74) *Attorney, Agent, or Firm* — HP Inc. Patent Department

(57) ABSTRACT

Asymmetrical 2,5-disubstituted-1,4-diaminobenzenes are provided, along with a process for forming both symmetrical and asymmetrical 2,5-disubstituted-1,4-diaminobenzenes.

12 Claims, 3 Drawing Sheets

2,5-DISUBSTITUTED-1,4-DIAMINOBENZENES

BACKGROUND 1,4-Diaminobenzene derivatives may be very useful oxidative dyes for a variety of applications. However, most substituted 1,4-diaminobenzene-based dyes are symmetrical 2,5-disubstituted-1,4-diaminobenzene derivatives, while the asymmetrical derivatives are very challenging to make. Not being able to make asymmetrical 2,5-disubstituted-1,4-diaminobenzene derivatives limits their applications due to the limited number of available choices of these types of dyes.

DETAILED DESCRIPTION

Figure 1:
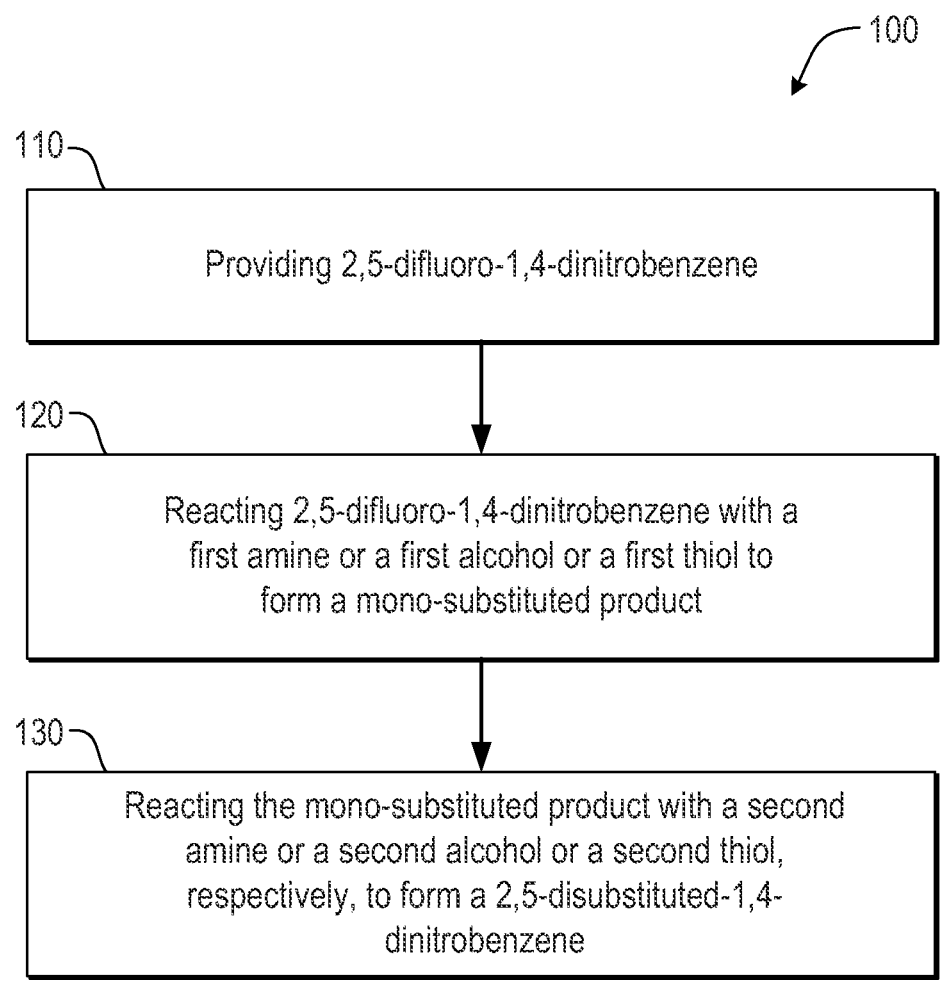
FIG. 1 is a flow chart depicting an example process for forming 2,5-disubstituted-1,4-dinitrobenzenes.

Reference is made now in detail to specific examples, which illustrates the best mode presently contemplated by the inventors for practicing the invention. Alternative examples are also briefly described as applicable.

It is to be understood that this disclosure is not limited to the particular process steps and materials disclosed herein because such process steps and materials may vary somewhat. It is also to be understood that the terminology used herein is used for the purpose of describing particular examples only. The terms are not intended to be limiting because the scope of the present disclosure is intended to be limited only by the appended claims and equivalents thereof.

It is noted that, as used in this specification and the appended claims, the singular forms "a," "an," and "the" include plural referents unless the context clearly dictates otherwise.

As used herein, a derivative is defined as is a compound that is derived from a similar compound by some chemical processes, usually containing essentially the basic structure of the parent substance.

As disclosed herein, a practical, novel, and inexpensive chemical process has been developed and is disclosed herein for a large scale synthesis of symmetrical and asymmetrical 2,5-disubstituted-1,4-diaminobenzene derivatives. Specific derivatives include 2,5-dinitro-substituted-1,4-diaminobenzenes and 2,5-dialkylamino-substituted-1,4-diaminobenzenes. The asymmetrical derivatives are also considered to be novel. While the term "asymmetrical" is employed herein, it will be appreciated that the equivalent term "unsymmetrical" could alternatively be employed.

As mentioned earlier, these 1,4-diaminobenzene derivatives are very useful oxidative dyes for a variety of applications. For example, both the asymmetrical and symmetrical derivatives may be used for optical data storage when co-used with a coupler, as described in greater detail below.

The general structure of 2,5-disubstituted-1,4-diaminobenzene derivatives is shown in Formula 1.

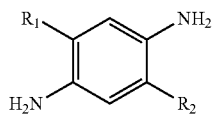

In Formula 1, $R_1$ and $R_2$ can be $R_3NH-$, $R_4R_5N-$, $R_6O-$ or $R_7S-$, where $R_3$, $R_4$, $R_5$, $R_6$, and $R_7$ may include, but are not limited to, substituted or unsubstituted hydrocarbon groups containing from 1 to 24 carbon atoms, branched aliphatic groups, linear lower aliphatic groups, cyclic aliphatic groups, homocyclic aryl groups, heterocyclic aryl groups, substituted derivatives thereof, and combinations thereof.

The substituted or unsubstituted hydrocarbon groups may be an alkyl group or an aryl group. Non-limiting examples of substituent groups that may be present on the aryl groups include alkyl groups, alkoxy groups, amino groups, substituted amino groups, acyl groups, acyloxy groups, amido groups, carboxyl groups, cyano groups, halogens, hydroxyl groups, nitro groups, sulfonyl groups, sulfinyl groups, sulfenyl groups, silyl groups, trifluoromethyl groups, and/or the like, and/or combinations thereof. Examples of aryl groups include, but are not limited to, acetylphenyl groups, acetamidophenyl groups, benzoyloxyphenyl groups, carboethoxyphenyl groups, carboxyphenyl groups, diphenyl fluorophenyl groups, difluorophenyl groups, ethoxyphenyl groups, hydroxyphenyl groups, methoxyethylphenyl groups, naphthyl groups, phenyl groups, phenoxyphenyl groups, trifluoromethyl-phenyl groups, tolyl groups, xylyl groups, and/or the like, and/or combinations thereof. Non-limiting examples of cyclic aryl derivatives include azulene groups, benzofuran groups, benzothiophene groups, benzimidazole groups, benzindazole groups, benzthiazole groups, cinnoline groups, carbazole groups, furan groups, indazole groups, imidazole groups, indene groups, isoxazole groups, isothiazole groups, isoquinoline groups, indolizine groups, indole groups, isoindole groups, indoline groups, naphthyridine groups, oxazole groups, oxadiazole groups, pyrazole groups, pyridine groups, pyrimidine groups, pyran groups, pyridazine groups, pyrazine groups, purine groups, phenanthrene groups, pteridine groups, phthalazine groups, pyrrole groups, quinoline groups, quinolizine groups, quinazoline groups, quinoxaline groups, thiazole groups, thiophene groups, triazole groups, thiadiazole groups, triazine groups, and/or the like, and/or combinations thereof.

Illustrative alkyl groups include, but are not limited to, methyl groups, ethyl groups, propyl groups, butyl groups, and/or the like, and/or combinations thereof. Non-limiting examples of cyclic alkyl groups include cyclopropyl groups, methylcyclopropyl groups, ethylcyclopropyl groups, propylcyclopropyl groups, butylcyclopropyl groups, cyclobutyl groups, methylcyclobutyl groups, ethylcyclobutyl groups, propylcyclobutyl groups, cyclopentyl groups, methylcyclopentyl groups, ethylcyclopentyl groups, propylcyclopentyl groups, cyclohexyl groups, methylcyclohexyl groups, ethylcyclohexyl groups, propylcyclohexyl groups, and/or the like, and/or combinations thereof.

In Formula 1, if $R_1=R_2$, then the derivative is considered to be a symmetrical compound. If $R_1 \neq R_2$, then the derivative is considered to be an asymmetrical compound.

Reactions 1A-1C illustrate the reaction of these substituted 2,5-disubstituted-1,4-diaminobenzene derivatives with a coupler to give possible new dyes 5, 7, 9. There are three major types of couplers based on colors obtained with the aromatic 1,4-diamines: blue coupler 4 (Reaction 1A), red coupler 6 (Reaction 1B), and yellow-green coupler 8 (Reaction 1C). The usual blue couplers 4 may include 1,3-diaminobenzene derivatives with the ability to couple at the 2,4-positions relative to the amino groups. Examples of blue couplers include N— and O-hydroxyethyl derivatives, dimeric couplers, and heterocyclic compounds. The principal red couplers 6 may include 3-aminophenol, 5-amino-2-methyl-phenol, and 1-naphthol. Yellow-green couplers 8 may include resorcinol, 4-cholroresorcinol, benzodioxoles, 2-methylresorcinol, and their derivatives.

Reaction Sequence 2

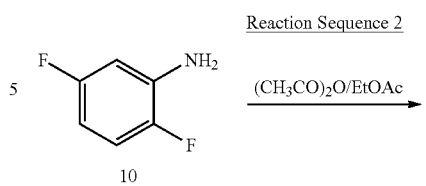

Reaction Series 1

[Reaction scheme showing compound 3 reacting with coupler 4 to form Indamine dye (blue) 5 via Reaction 1A; with coupler 6 to form Indoaniline dye (magenta) 7 via Reaction 1B; and with coupler 8 to form Indoaniline dye (yellow-green) 9 via Reaction 1C]

In Reactions 1A-1C, the groups $R_1$ and $R_2$ may include, but are not limited to, substituted or unsubstituted hydrocarbon groups containing from 1 to 24 carbon atoms, branched aliphatic groups, linear lower aliphatic groups, cyclic aliphatic groups, homocyclic aryl groups, heterocyclic aryl groups, substituted derivatives thereof, or combinations thereof, as described above.

The innovative synthesis of such asymmetrical substituted 1,4-diaminobenzene based dyes are described below as one of the examples. A novel way to synthesize 2,5-difluoro-1,4-dinitrobenzene 14 is shown in Reaction Sequence 2; the intermediate compound 14 is an important intermediate for the synthesis of 2,5-disubstituted-1,4-diaminobenzene derivatives.

-continued

[Structure 11: F-substituted NHCOCH₃ aniline] → Fuming HNO₃/0° C.

[Structure 12: O₂N, F, NHCOCH₃ substituted benzene] → Con. HCl/EtOH reflux

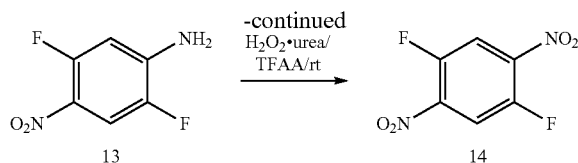

In the synthesis of the intermediate compound 14, reaction of commercially-available 2,5-difluoroaniline 10 with acetic anhydride gave compound 11, which was nitrated with fuming nitric acid at low temperature to give compound 12. Deprotection of compound 12 in a concentrated hydrochloric acid/ethanol solution (HCl/EtOH) gave 2,5-difluoro-4-nitroaniline 13 in a very good yield. Oxidation of the amino group to the corresponding nitro group was achieved by use of $H_2O_2$-urea in trifluoroacetic anhydride (TFAA), giving the desired target 2,5-difluoro-1,4-dinitrobenzene 14 in a reasonable yield.

Then a nucleophilic substitution reaction between 2,5-difluoro-1,4-dinitrobenzene 14 and propyl amine was carried out, as shown in Reactions 3A-3C.

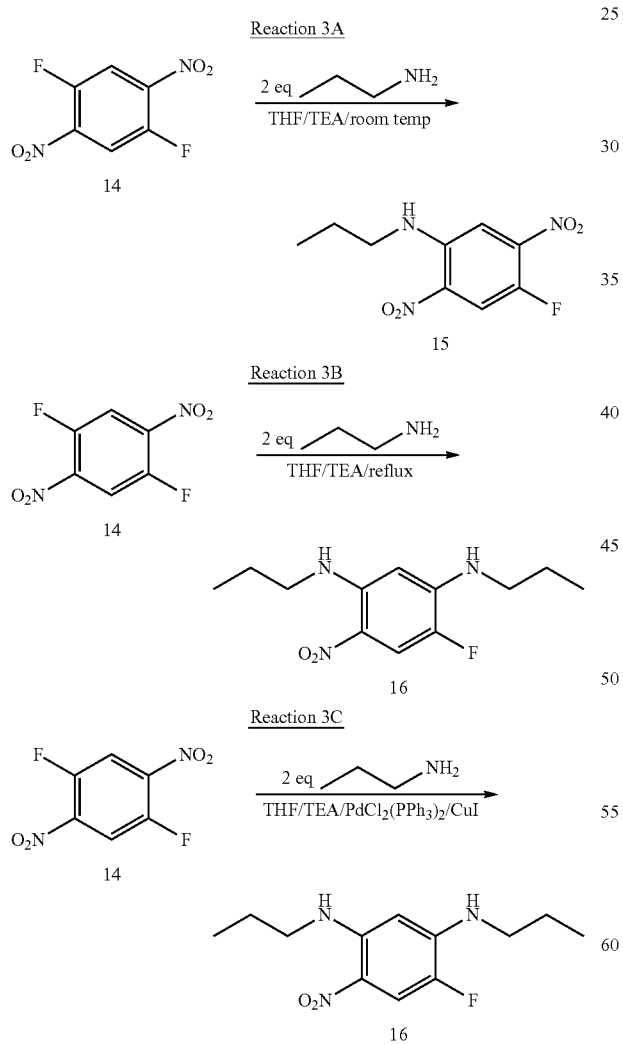

Reaction of compound 14 with an appropriate amount of propylamine, e.g., 2 equivalents (eq), of propylamine at room temperature only gave monopropyl substituted product 15 (Reaction 3A). When the same reaction was carried out under reflux, a denitration substitution reaction took place and a dipropyl substituted product 16 was obtained (Reaction 3B). Similarly, palladium-catalyzed reaction of compound 14 with 2 eq of propylamine at room temperature also gave the denitration substitution product 16 (Reaction 3C).

Without subscribing to any particular theory, it appears that introduction of the first propylamino group on the benzene ring deactivated the second fluoro atom on the benzene ring. Based on this theory, this synthetic technology may be useful for making both symmetrical and asymmetrical 2,5-disubstituted-1,4-diaminobenzene derivatives as shown in Reaction Sequences 4 and 5.

Reaction Sequence 4 shows a general approach to make 1,4-diaminobenzene derivatives with 2,5-positions substituted with two primary amines ($R_1$—NH— and $R_2$—NH—).

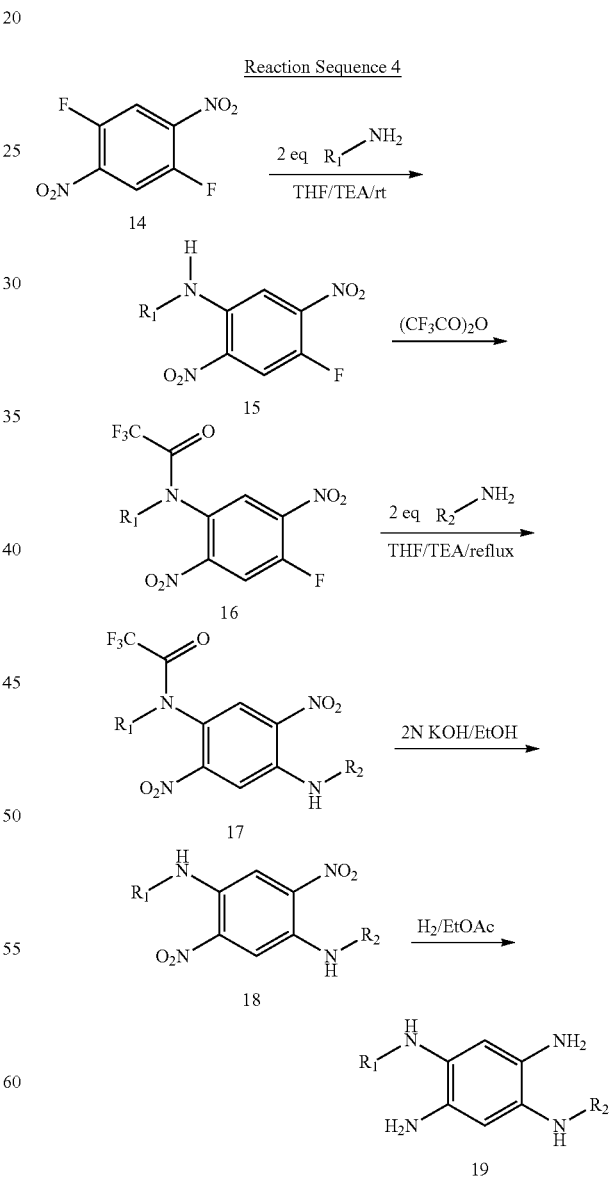

Reaction of 2,5-difluoro-1,4-dinitrobenzene 14 with an appropriate amount, e.g., 2 eq, of propylamine afforded mono-substituted product 15. Protection of the propylamino group of compound 15 with a trifluoroacetyl group gave compound 16, which was reacted with an appropriate amount, e.g., 2 eq, of butylamine to give the desired 2-butylamino-5-propylamino substituted product 17 without a denitration reaction taking place. Deprotection of compound 17 afforded the desired 2-butylamino-5-propylamino-1,4-dinitrobenzene 18. Reduction of compound 18 by hydrogenation in ethyl acetate in the presence of 10% Pd/C gave the desired 1,4-diamino-2-butylamino-5-propylamino benzene 19. By using this method and different nucleophiles, one may obtain a large number of both symmetrical and asymmetrical 2,5-disubstituted-1,4-diaminobenzene-based dyes. To obtain symmetrical 2,5-disubstituted-1,4-diaminobenzene dyes, the first and second primary amines are the same. To obtain asymmetrical 2,5-disubstituted-1,4-diaminobenzene dyes, the first and second primary amines are different.

In the reactions depicted in Reaction Sequence 4, $R_1$ and $R_2$ may include, but are not limited to, substituted or unsubstituted hydrocarbon groups containing from 1 to 24 carbon atoms, branched aliphatic groups, linear lower aliphatic groups, cyclic aliphatic groups, homocyclic aryl groups, heterocyclic aryl groups, substituted derivatives thereof, or combinations thereof. Where $R_1=R_2$, a symmetrical 2,5-disubstituted-1,4-diaminobenzene dye is formed. Otherwise, an asymmetrical 2,5-disubstituted-1,4-diaminobenzene dye is formed.

The substituted or unsubstituted hydrocarbon groups may be an alkyl group or an aryl group. Non-limiting examples of substituent groups that may be present on the aryl groups include alkyl groups, alkoxy groups, amino groups, substituted amino groups, acyl groups, acyloxy groups, amido groups, carboxyl groups, cyano groups, halogens, hydroxyl groups, nitro groups, sulfonyl groups, sulfinyl groups, sulfenyl groups, silyl groups, trifluoromethyl groups, and/or the like, and/or combinations thereof. Examples of aryl groups include, but are not limited to, acetylphenyl groups, acetamidophenyl groups, benzoyloxyphenyl groups, carboethoxyphenyl groups, carboxyphenyl groups, diphenyl fluorophenyl groups, difluorophenyl groups, ethoxyphenyl groups, hydroxyphenyl groups, methoxyethylphenyl groups, naphthyl groups, phenyl groups, phenoxyphenyl groups, trifluoromethyl-phenyl groups, tolyl groups, xylyl groups, and/or the like, and/or combinations thereof. Non-limiting examples of cyclic aryl derivatives include azulene groups, benzofuran groups, benzothiophene groups, benzimidazole groups, benzindazole groups, benzthiazole groups, cinnoline groups, carbazole groups, furan groups, indazole groups, imidazole groups, indene groups, isoxazole groups, isothiazole groups, isoquinoline groups, indolizine groups, indole groups, isoindole groups, indoline groups, naphthyridine groups, oxazole groups, oxadiazole groups, pyrazole groups, pyridine groups, pyrimidine groups, pyran groups, pyridazine groups, pyrazine groups, purine groups, phenanthrene groups, pteridine groups, phthalazine groups, pyrrole groups, quinoline groups, quinolizine groups, quinazoline groups, quinoxaline groups, thiazole groups, thiophene groups, triazole groups, thiadiazole groups, triazine groups, and/or the like, and/or combinations thereof.

Illustrative alkyl groups include, but are not limited to, methyl groups, ethyl groups, propyl groups, butyl groups, and/or the like, and/or combinations thereof. Non-limiting examples of cyclic alkyl groups include cyclopropyl groups, methylcyclopropyl groups, ethylcyclopropyl groups, propylcyclopropyl groups, butylcyclopropyl groups, cyclobutyl groups, methylcyclobutyl groups, ethylcyclobutyl groups, propylcyclobutyl groups, cyclopentyl groups, methylcyclopentyl groups, ethylcyclopentyl groups, propylcyclopentyl groups, cyclohexyl groups, methylcyclohexyl groups, ethylcyclohexyl groups, propylcyclohexyl groups, and/or the like, and/or combinations thereof.

Reaction Sequence 5 shows a general approach to make 1,4-diaminobenzene derivatives with the 2,5-positions substituted with two secondary amines ($R_1(R_2)N$— and $R_3(R_4)N$—).

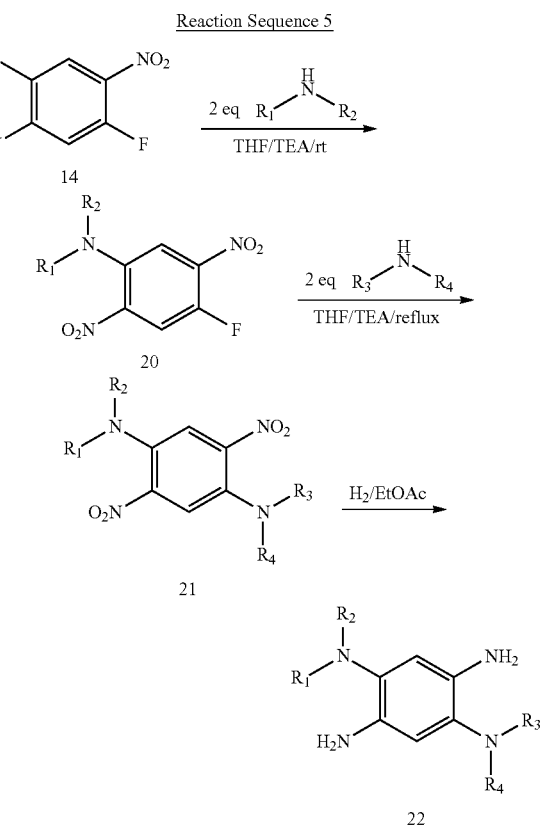

Reaction of 2,5-difluoro-1,4-dinitrobenzene 14 with an appropriate amount, e.g., 2 eq, of secondary amine $R_1(R_2)$NH affords mono-substituted product 20. Reaction of product 20 with an appropriate amount, e.g., 2 eq, of secondary amine $R_3(R_4)$NH gives the desired 1,4-dinitrobenzene 22 with 2,5-positions substituted with two different secondary amines ($R_1(R_2)N$— and $R_3(R_4)N$—). Reduction of compound 22 by hydrogenation in ethyl acetate in the presence of 10% Pd/C gives the desired 1,4-diaminobenzene derivatives 22 with 2,5-positions substituted with two different secondary amines ($R_1(R_2)N$— and $R_3(R_4)N$—). By using this method and different nucleophiles, one may obtain a large number of both symmetrical and asymmetrical 2,5-disubstituted-1,4-diaminobenzene based dyes. To obtain symmetrical 2,5-disubstituted-1,4-diaminobenzene dyes, the first and second secondary amines are the same. To obtain asymmetrical 2,5-disubstituted-1,4-diaminobenzene dyes, the first and second secondary amines are different.

In Reaction Sequence 5, $R_1$, $R_2$, $R_3$, and $R_4$ may include, but are not limited to, substituted or unsubstituted hydrocarbon groups containing from 1 to 24 carbon atoms, branched aliphatic groups, linear lower aliphatic groups, cyclic aliphatic groups, homocyclic aryl groups, heterocyclic aryl groups, substituted derivatives thereof, or combinations thereof. Where $R_1=R_3$ and $R_2=R_4$ (or, equivalently, $R_1=R_4$ and $R_2=R_3$), a symmetrical 2,5-disubstituted-1,4-diaminobenzene dye is formed. Otherwise, an asymmetrical 2,5-disubstituted-1,4-diaminobenzene dye is formed.

The substituted or unsubstituted hydrocarbon groups may be an alkyl group or an aryl group. Non-limiting examples of substituent groups that may be present on the aryl groups include alkyl groups, alkoxy groups, amino groups, substituted amino groups, acyl groups, acyloxy groups, amido groups, carboxyl groups, cyano groups, halogens, hydroxyl groups, nitro groups, sulfonyl groups, sulfinyl groups, sulfenyl groups, silyl groups, trifluoromethyl groups, and/or the like, and/or combinations thereof. Examples of aryl groups include, but are not limited to, acetylphenyl groups, acetamidophenyl groups, benzoyloxyphenyl groups, carboethoxyphenyl groups, carboxyphenyl groups, diphenyl fluorophenyl groups, difluorophenyl groups, ethoxyphenyl groups, hydroxyphenyl groups, methoxyethylphenyl groups, naphthyl groups, phenyl groups, phenoxyphenyl groups, trifluoromethyl-phenyl groups, tolyl groups, xylyl groups, and/or the like, and/or combinations thereof. Non-limiting examples of cyclic aryl derivatives include azulene groups, benzofuran groups, benzothiophene groups, benzimidazole groups, benzindazole groups, benzthiazole groups, cinnoline groups, carbazole groups, furan groups, indazole groups, imidazole groups, indene groups, isoxazole groups, isothiazole groups, isoquinoline groups, indolizine groups, indole groups, isoindole groups, indoline groups, naphthyridine groups, oxazole groups, oxadiazole groups, pyrazole groups, pyridine groups, pyrimidine groups, pyran groups, pyridazine groups, pyrazine groups, purine groups, phenanthrene groups, pteridine groups, phthalazine groups, pyrrole groups, quinoline groups, quinolizine groups, quinazoline groups, quinoxaline groups, thiazole groups, thiophene groups, triazole groups, thiadiazole groups, triazine groups, and/or the like, and/or combinations thereof.

Illustrative alkyl groups include, but are not limited to, methyl groups, ethyl groups, propyl groups, butyl groups, and/or the like, and/or combinations thereof. Non-limiting examples of cyclic alkyl groups include cyclopropyl groups, methylcyclopropyl groups, ethylcyclopropyl groups, propylcyclopropyl groups, butylcyclopropyl groups, cyclobutyl groups, methylcyclobutyl groups, ethylcyclobutyl groups, propylcyclobutyl groups, cyclopentyl groups, methylcyclopentyl groups, ethylcyclopentyl groups, propylcyclopentyl groups, cyclohexyl groups, methylcyclohexyl groups, ethylcyclohexyl groups, propylcyclohexyl groups, and/or the like, and/or combinations thereof.

Reaction Sequence 6 shows a general approach to make 1,4-diaminobenzene derivatives with 2,5-positions substituted with two different alcohols or thiols ($R_1O-$, $R_2O-$ or $R_1S-$, $R_2S-$).

Reaction Sequence 6

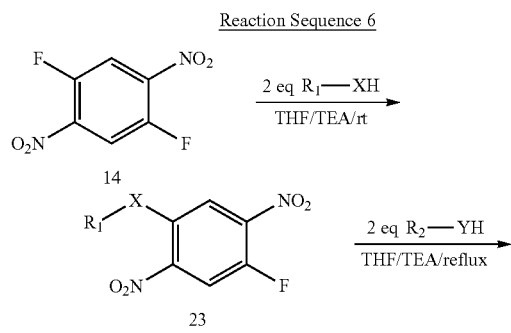

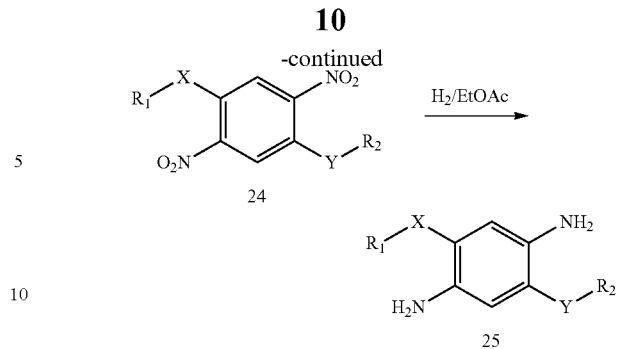

Reaction of 2,5-difluoro-1,4-dinitrobenzene 14 with an appropriate amount, e.g., 2 eq, of the first alcohol or thiol $R_1-XH$ affords mono-substituted product 23. Reaction of 23 with an appropriate amount, e.g., 2 eq, of the second alcohol or thiol $R_2-YH$ gives the desired 1,4-dinitrobenzene 24 with the 2,5-positions substituted with two different alcohols or thiols ($R_1O-$, $R_2O-$ or $R_1S-$, $R_2S-$). Reduction of compound 24 by hydrogenation in ethyl acetate in the presence of 10% Pd/C gives the desired 1,4-diaminobenzene derivatives 25 with 2,5-positions substituted with two different alcohols or thiols ($R_1O-$, $R_2O-$ or $R_1S-$, $R_2S-$). By using this method and different nucleophiles, one may obtain a large number of both symmetrical and asymmetrical 2,5-disubstituted-1,4-diaminobenzene based dyes. To obtain symmetrical 2,5-disubstituted-1,4-diaminobenzene dyes, the first and second alcohols (or thiols) are the same. To obtain asymmetrical 2,5-disubstituted-1,4-diaminobenzene dyes, the first and second alcohols (or thiols) are different.

In Reaction Sequence 6, X and Y can be O or S. Further, both X and Y can be O, both X and Y can be S, and one of X and Y can be O and the other S.

$R_1$ and $R_2$ may include, but are not limited to, substituted or unsubstituted hydrocarbon groups containing from 1 to 24 carbon atoms, branched aliphatic groups, linear lower aliphatic groups, cyclic aliphatic groups, homocyclic aryl groups, heterocyclic aryl groups, substituted derivatives thereof, or combinations thereof. Where $R_1=R_2$, a symmetrical 2,5-disubstituted-1,4-diaminobenzene dye is formed. Where $R_1 \ne R_2$, an asymmetrical 2,5-disubstituted-1,4-diaminobenzene dye is formed.

The substituted or unsubstituted hydrocarbon groups may be an alkyl group or an aryl group. Non-limiting examples of substituent groups that may be present on the aryl groups include alkyl groups, alkoxy groups, amino groups, substituted amino groups, acyl groups, acyloxy groups, amido groups, carboxyl groups, cyano groups, halogens, hydroxyl groups, nitro groups, sulfonyl groups, sulfinyl groups, sulfenyl groups, silyl groups, trifluoromethyl groups, and/or the like, and/or combinations thereof. Examples of aryl groups include, but are not limited to, acetylphenyl groups, acetamidophenyl groups, benzoyloxyphenyl groups, carboethoxyphenyl groups, carboxyphenyl groups, diphenyl fluorophenyl groups, difluorophenyl groups, ethoxyphenyl groups, hydroxyphenyl groups, methoxyethylphenyl groups, naphthyl groups, phenyl groups, phenoxyphenyl groups, trifluoromethyl-phenyl groups, tolyl groups, xylyl groups, and/or the like, and/or combinations thereof. Non-limiting examples of cyclic aryl derivatives include azulene groups, benzofuran groups, benzothiophene groups, benzimidazole groups, benzindazole groups, benzthiazole groups, cinnoline groups, carbazole groups, furan groups, indazole groups, imidazole groups, indene groups, isoxazole groups, isothiazole groups, isoquinoline groups, indolizine groups, indole groups, isoindole groups, indoline groups, naphthyridine groups, oxazole groups, oxadiazole groups, pyrazole groups, pyridine groups, pyrimidine groups, pyran groups, pyridazine groups, pyrazine groups, purine groups, phenanthrene groups, pteridine groups, phthalazine groups, pyrrole groups, quinoline groups, quinolizine groups, quinazoline groups, quinoxaline groups, thiazole groups, thiophene groups, triazole groups, thiadiazole groups, triazine groups, and/or the like, and/or combinations thereof.

Illustrative alkyl groups include, but are not limited to, methyl groups, ethyl groups, propyl groups, butyl groups, and/or the like, and/or combinations thereof. Non-limiting examples of cyclic alkyl groups include cyclopropyl groups, methylcyclopropyl groups, ethylcyclopropyl groups, propylcyclopropyl groups, butylcyclopropyl groups, cyclobutyl groups, methylcyclobutyl groups, ethylcyclobutyl groups, propylcyclobutyl groups, cyclopentyl groups, methylcyclopentyl groups, ethylcyclopentyl groups, propylcyclopentyl groups, cyclohexyl groups, methylcyclohexyl groups, ethylcyclohexyl groups, propylcyclohexyl groups, and/or the like, and/or combinations thereof.

A specific example of the synthesis of 1,4-diamino-2-butylamino-5-propylamino benzene is shown in Reaction Sequence 7.

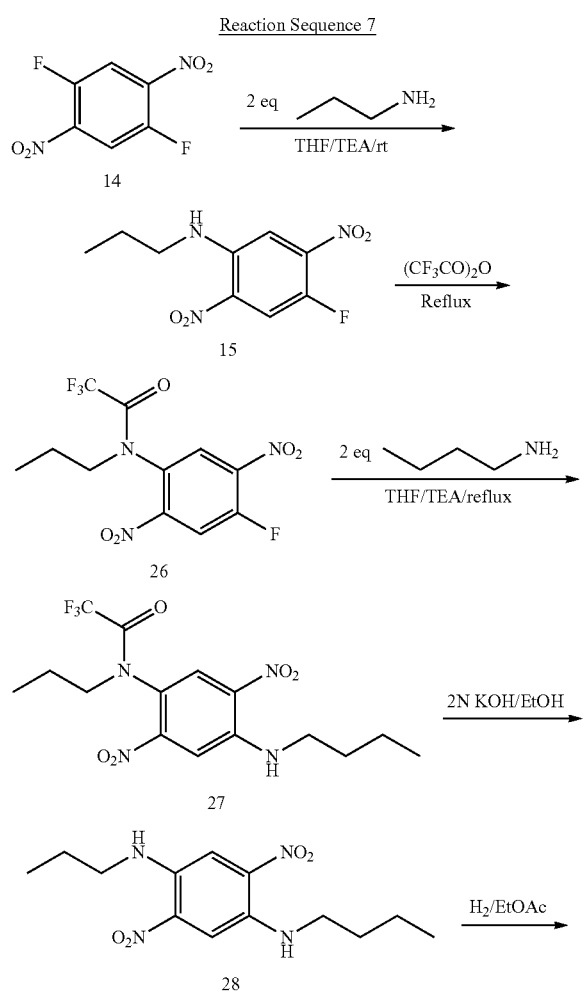

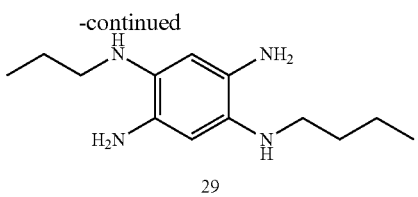

The reaction of 2,5-difluoro-1,4-dinitrobenzene 14 with an appropriate amount, e.g., 2 eq, of propylamine afforded mono-substituted product 15. Protection of the propylamino group of compound 15 with a trifluoroacetyl group gave compound 26, which reacted with an appropriate amount, e.g., 2 eq, of butylamine to give the desired 2-butylamino-5-propylamino-substituted-1,4-dinitrobenzene product 27 without a denitration reaction taking place. Deprotection of compound 27 afforded the desired 2-butylamino-5-propylamino-1,4-dinitrobenzene 28. Reduction of compound 28 by hydrogenation in ethyl acetate in the presence of 10% Pd/C gave the desired 1,4-diamino-2-butylamino-5-propylamino benzene 29. By using this method and different nucleophiles, one may obtain a large number of both symmetrical and asymmetrical 2,5-disubstituted-1,4-diaminobenzene based dyes.

Figure 2:
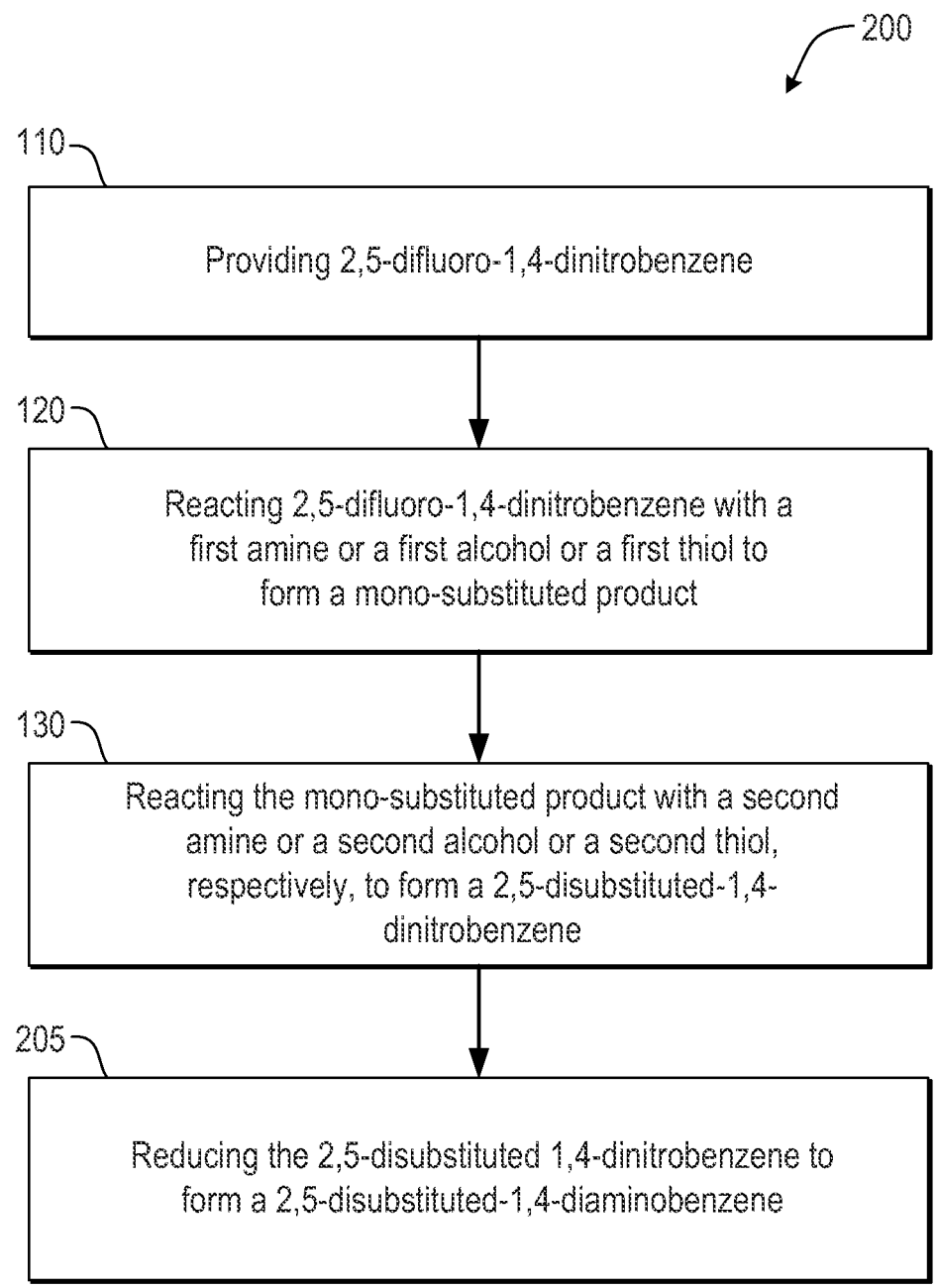
FIG. 2 is a flow chart depicting an example process for forming 2,5-disubstituted-1,4-diaminobenzenes.
Figure 3:
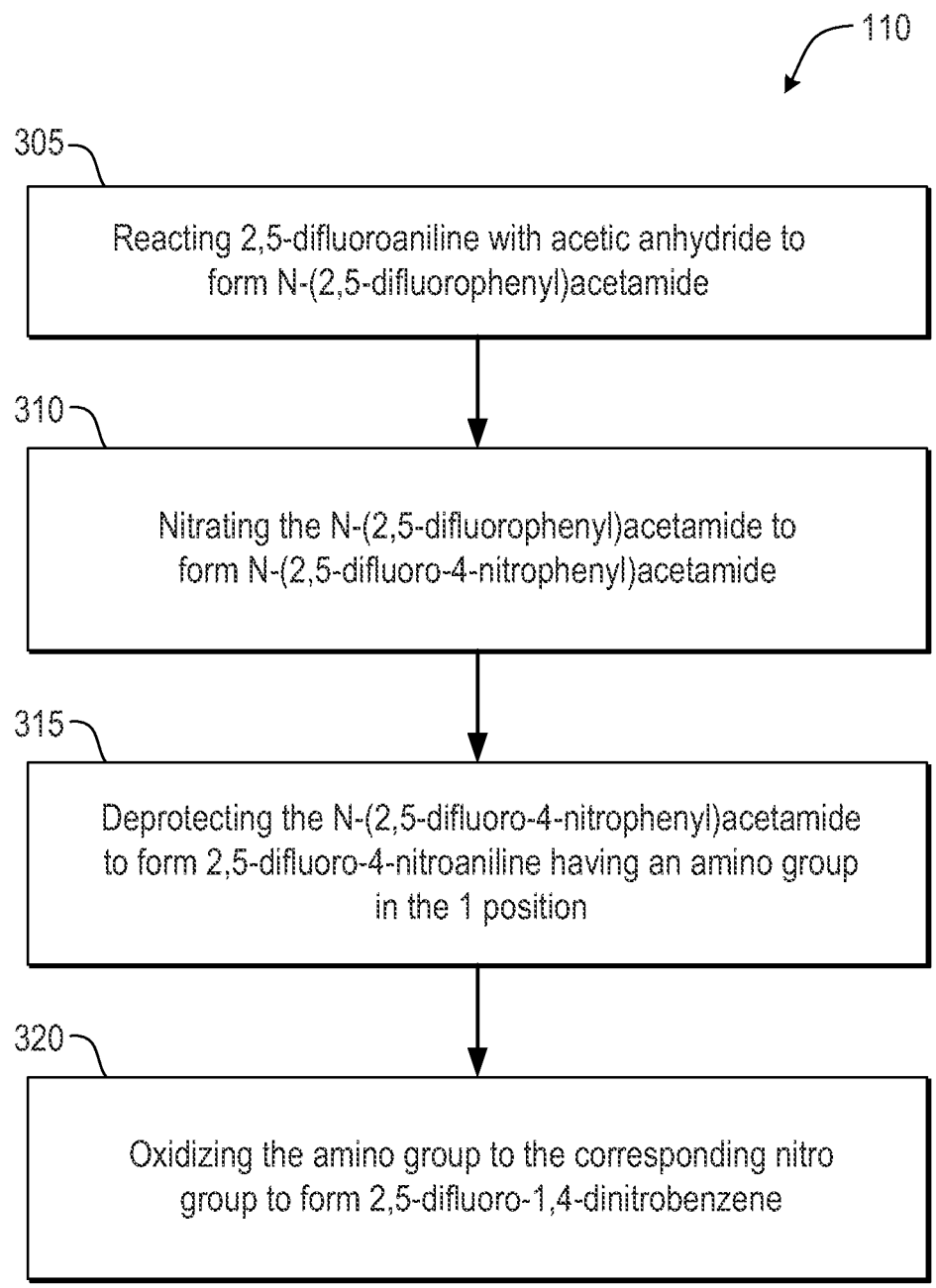
FIG. 3 is a flow chart depicting an example process for forming 2,5-difluoro-1,4-dinitrobenzene, an intermediate useful for producing 2,5-disubstituted-1,4-diaminobenzenes and 2,5-disubstituted-1,4-dinitrobenzenes.

FIGS. 1-3 are flow charts that illustrate example processes employed in the practice of the teachings herein.

FIG. 1 depicts a process 100 for preparing 2,5-disubstituted-1,4-dinitrobenzenes. The process 100 includes providing 110 2,5-difluoro-1,4-dinitrobenzene. The process 100 further includes reacting 120 2,5-difluoro-1,4-dinitrobenzene with a first amine or a first alcohol or a first thiol to form a mono-substituted product. The process 100 concludes with reacting 130 the mono-substituted product with a second amine or a second alcohol or a second thiol, respectively, to form a 2,5-disubstituted-1,4-dinitrobenzene.

FIG. 2 depicts a process 200 for preparing 2,5-disubstituted-1,4-diaminobenzenes. The process 200 includes the process described for FIG. 1 and additionally includes reducing 205 the 2,5-disubstituted-1,4-dinitrobenzene to form a 2,5-disubstituted-1,4-diaminobenzene.

FIG. 3 depicts a process 110 for preparing 2,5-difluoro-1,4-dinitrobenzene, used in the processes depicted in FIGS. 1 and 2. The process 110 includes reacting 305 2,5-difluoroaniline with acetic anhydride to form N-(2,5-difluorophenyl)acetamide. The process 110 further includes nitrating 310 the N-(2,5-difluorophenyl)acetamide to form N-(2,5-difluoro-4-nitrophenyl)acetamide. The process 110 further includes deprotecting 315 the N-(2,5-difluoro-4-nitrophenyl)acetamide to form 2,5-difluoro-4-nitroaniline having an amino group in the 1 position. The process 110 concludes with oxidizing 320 the amino group to the corresponding nitro group to form 2,5-difluoro-1,4-dinitrobenzene.

The foregoing description has been directed to forming 2,5-dinitro compounds, 2,5-dialkylamino compounds, 2,5-dialcohol compounds, and 2,5-dithiol compounds. Based on the foregoing description, it will be appreciated that any of a nitro, alkylamino, alcohol, and thiol can be in one of the 2,5 positions and that any of a nitro, alkylamino, alcohol, and thiol can be in the other of the 2,5 positions.

In summary, a practical and inexpensive chemical process has been developed for a large scale synthesis of symmetrical and asymmetrical 2,5-disubstituted-1,4-diaminobenzene derivatives. These could lead to a large number of new dyes when reacting with different couplers as shown in FIG. 1, for example.

EXAMPLES

Example 1

Synthesis of N-(2,5-difluorophenyl)acetamide 11.

To a solution of 2,5-difluoroaniline 10 (30.72 g, 238 mmol) in 100 ml of dichloromethane was added acetic anhydride (29.15 g, 285 mmol) at room temperature. The resulting mixture was stirred at room temperature overnight. The volatile solvent was evaporated, and water (200 ml) was added. A white solid was collected by filtration and dried in vacuum, giving the desired product 11 as a white solid, 40 g (100%).

$^1$H NMR (300 MHZ, CDCl$_3$) δ 8.16 (m, 1 H), 7.42 (brs, 1H), 7.01 (m, 1 H), 6.72 (m, 1H), 2.22 (s, 3 H).

Example 2

Synthesis of N-(2,5-difluoro-4-nitrophenyl)acetamide 12.

To a stirred fuming nitric acid (90 mL) was added portion wise N-(2,5-difluorophenyl)acetamide 11 (34.2 g, 0.2 mol) at 0° C. The resulting solution was stirred at 0° C. for 3 hours. The solution was poured into ice-water mixture. The resulting yellow solid was collected by filtration and washed with more water (3×50 mL), dried in vacuum, giving rise to the desired N-(2,5-difluoro-4-nitrophenyl)acetamide 12 as a pale yellow solid: 38.0 g (88%).

$^1$H NMR (300 MHZ, DMSO-d$_6$) δ 10.45 (s, 1 H), 8.33 (dd, J$_1$=6.3 Hz, J$_2$=14.1 Hz, 1H), 8.19 (dd, J$_1$=6.3 Hz, J$_2$=14.1 Hz, 1H), 2.18 (s, 3 H).

Example 3

Synthesis of 2,5-difluoro-4-nitroaniline 13.

A suspension of N-(2,5-difluoro-4-nitrophenyl)acetamide 12 (38 g, 176 mmol) in 150 mL of concentrated HCl aqueous solution and 150 mL of ethanol was heated to reflux for 3 hours. After cooling down to room temperature, the volatile solvent was evaporated and more water (150 mL) was added and stirred for another 2 hours. The resulting deep yellow solid was collected by filtration and dried in vacuum, giving the desired product 13 as a yellow solid, 22.6 g (74%).

$^1$H NMR (300 MHZ, DMSO-d$_6$) δ 7.87 (dd, J$_1$=6.3 Hz, J$_2$=14.1 Hz, 1H), 7.07 (brs, 2 H), 6.60 (dd, J$_1$=6.3 Hz, J$_2$=14.1 Hz, 1H).

Example 4

Synthesis of 2,5-difluoro-1,4-dinitrobenzene 14.

To a solution of hydrogen peroxide-urea complex (48.0 g, 0.51 mol) in 350 mL of dichloromethane was added trifluoroacetic anhydride (105 mL) at 0° C. After the exothermic reaction subsided, then 2,5-difluoro-4-nitroaniline 13 (22.2 g, 127.5 mmol) was added portion wise over a period of 1 hour. After the addition, the resulting solution was stirred at room temperature for overnight. Then the solution was washed with water (3×100 mL) and dried over sodium sulfate. Sodium sulfate was removed by filtration and the filtrate was evaporated to give a crude product, which was further purified by recrystallization from 95% ethanol, giving the desired product 14 as a brown solid, 13.05 g (50%).

$^1$H NMR (300 MHZ, DMSO-d$_6$) δ 8.57 (m, 2 H).

Example 5

Synthesis of 4-fluoro-2,5-dinitro-N-propylbenzeneamine 15.

To a solution of 2,5-difluoro-1,4-dinitrobenzene 14 (612 mg, 3.0 mmol) in 20 ml of tetrahydrofuran (THF) was added propylamine (266 mg, 4.5 mmol) at room temperature under N$_2$. The resulting solution was stirred at room temperature for overnight. The volatile solvent was evaporated to give a crude product, which was further purified by flash chromatography to give the desired product 15 as a purple solid: 687 mg (100%).

$^1$H NMR (300 MHZ, CDCl$_3$) δ 8.12 (d, J=10.8 Hz, 1 H), 7.85 (brs, 1H), 7.46 (d, J=6 Hz, 1 H), 3.32 (m, 2 H), 1.81 (m, 2 H), 1.08 (m, 3 H).

Example 6

Synthesis of N-1,N-5-dipropyl-4-fluoro-2-nitrobenzenediamine 16.

To a solution of 2,5-difluoro-1,4-dinitrobenzene 14 (408 mg, 2.0 mmol) in 20 ml of tetrahydrofuran (THF) was added propylamine (266 mg, 4.5 mmol) at room temperature under N$_2$. The resulting solution was stirred under reflux for overnight. The volatile solvent was evaporated to give a crude product, which was further purified by flash chromatography to give the desired product 16 as a brown solid: 536 mg (95%).

$^1$H NMR (300 MHZ, CDCl$_3$) δ 8.6.0 (brs, 1 H), 7.82 (d, J=12.6 Hz, 1H), 5.66 (d, J=7.5 Hz, 1 H), 4.65 (brs, 1 H), 3.21 (m, 4 H), 1.74 (m, 4H), 1.07 (m, 6 H).

Example 7

Synthesis of N-1,N-5-dipropyl-4-fluoro-2-nitrobenzenediamine 16.

To a solution of 2,5-difluoro-1,4-dinitrobenzene 14 (408 mg, 2.0 mmol) in 15 ml of tetrahydrofuran (THF) was added bis(triphenylphosphine)palladium dichloride (PdCl$_2$(PPh$_3$)$_2$, 50 mg, 0.07 mmol), copper (I) iodide (40 mg, 0.2 mmol), and propylamine (296 mg, 5.0 mmol) at room temperature under N$_2$. The resulting solution was stirred at room temperature for overnight. The volatile solvent was evaporated to give a crude product, which was further purified by flash chromatography to give the desired product 16 as a brown solid: 254 mg (90%).

$^1$H NMR (300 MHZ, CDCl$_3$) δ 8.6.0 (brs, 1 H), 7.82 (d, J=12.6 Hz, 1H), 5.66 (d, J=7.5 Hz, 1 H), 4.65 (brs, 1 H), 3.21 (m, 4 H), 1.74 (m, 4H), 1.07 (m, 6 H).

Example 8

Synthesis of 4-fluoro-2,5-dinitro-N-propyl-N-trifluoroacetylbenzeneamine 26.

A mixture of 4-fluoro-2,5-dinitro-N-propylbenzeneamine 15 (700 mg, 3.0 mmol) in 10 mL of trifluoroacetic anhydride was refluxed for 8 hours. After cooling to room temperature, the volatile solvent was evaporated. The residue was dissolved into 50 mL of dichloromethane, washed with saturated sodium bicarbonate aqueous solution, dried over sodium sulfate. Evaporation of solvent gave the desired product 26: 936 mg (96%).

$^1$H NMR (300 MHZ, CDCl$_3$) δ 8.12 (m, 2 H), 4.22 (m, 2 H), 3.20 (m, 2 H), 0.96 m, 3 H).

Example 9

Synthesis of N-2,5-dinitro-4-butylaminophenyl-N-propyl-2,2,2-trifluoroacetamide 27.

To a solution of 4-fluoro-2,5-dinitro-N-propyl-N-trifluoroacetylbenzeneamine 26 (975 mg, 3.0 mmol) in 15 mL of tetrahydrofuran (THF) was added butylamine (324 mg, 4.5 mmol) and triethylamine (TEA, 455 mg, 4.5 mmol) at room temperature. The resulting solution was stirred under reflux overnight. The volatile solvent was evaporated to give a crude product, which was further purified by flash chromatography to give the desired product 27 as a yellow solid: 1.128 g (100%).

$^1$H NMR (300 MHZ, CDCl$_3$) δ 8.25 (s, 1 H), 8.17 (s, 1 H), 7.55 (s, 1 H), 4.18 (m, 2 H), 3.38 (m, 2 H), 3.15 (m, 2 H), 1.85 (m, 4 H), 1.08 (m, 4 H), 1.08 (m, 3 H), 0.95 (m, 3 H).

Example 10

Synthesis of 1,4-dinitro-2-propylamino-5-butylaminobenzene 28.

To a solution of N-2,5-dinitro-4-butylaminophenyl-N-propyl-2,2,2-trifluoroacetamide 27 (1.13 g, 3.0 mmol) in 15 ml of ethanol was added 2 N potassium hydroxide aqueous solution (3 mL, 6.0 mmol) at room temperature. The resulting mixture was stirred at room temperature for overnight. The volatile solvent was evaporated, and water (50 ml) was added. A dark blue solid was collected by filtration and dried in vacuum, giving the desired product 28: 700 mg (83%).

$^1$H NMR (300 MHZ, CDCl$_3$) δ 7.68 (s, 2 H), 6.98 (m, 2 H), 3.23 (m, 4 H), 1.75 (m, 6 H), 1.06 (t, J=7.8 Hz, 6 H).

Example 11

Synthesis of 1,4-diamino-2-propylamino-5-butylaminobenzene 29.

A mixture of 1,4-dinitro-2-propylamino-5-butylamino benzene 28 (592 mg, 2 mmol) and 10% Pd/C (150 mg, 20%) in 50 mL of ethyl acetate was hydrogenated at 55 psi for 48 hours. The catalyst was removed through a column of celite under Ar and washed with more ethyl acetate (100 mL). Evaporation of solvent gave the desired product 29 as a brown solid: 532 mg, 90% yield.

$^1$H NMR (300 MHZ, CDCl$_3$) δ 5.24 (s, 2 H), 3.08 (t, J=7.2 Hz, 4H), 1.69 (m, 6 H), 0.99 (t, J=7.5 Hz, 6H).

In summary, a practical and inexpensive chemical process has been developed for a large scale synthesis of symmetrical and asymmetrical 2,5-disubstituted-1,4-diaminobenzene derivatives. These could lead to a large number of new dyes when reacting with different couplers, such as shown in Reactions 1A-1C.

These form a totally new series of asymmetrical 2,5-disubstituted-1,4-diaminobenzenes and no known methods for preparing them existed before. The methods disclosed herein provide a novel and unique technology to prepare both symmetrically and asymmetrically substituted-1,4-diaminobenzene based dyes. Reacting these novel dyes with various couplers may lead to large number of new dyes.

What is claimed is:

1. A composition comprising 2,5-disubstituted-1,4-diaminobenzenes wherein at least 90% of the 2,5-disubstituted-1,4-diaminobenzenes are asymmetrical.

2. The composition of claim 1, wherein the 2,5-disubstituted-1,4-diaminobenzenes comprise 2,5-dinitro-substituted-1,4-diaminobenzenes.

3. The composition of claim 1 wherein the asymmetrical 2,5-disubstituted-1,4-diaminobenzenes are 2,5-dialkylamino-substituted-1,4-diaminobenzenes.

4. The composition of claim 1 wherein the asymmetrical 2,5-disubstituted-1,4-diaminobenzenes have the general formula

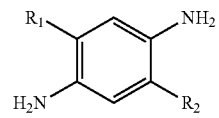

where $R_1$ and $R_2$ are different, wherein $R_1$ and $R_2$ are each selected from the group consisting of $R_3NH-$, $R_4R_5N-$, $R_6O-$, and $R_7S-$, where $R_3$, $R_4$, $R_5$, $R_6$, and $R_7$ are each independently selected from the group consisting of substituted and unsubstituted hydrocarbon groups containing from 1 to 24 carbon atoms, branched aliphatic groups, linear lower aliphatic groups, cyclic aliphatic groups, homocyclic aryl groups, and heterocyclic aryl groups.

5. A process for preparing the composition of claim 1, the process including:
providing 2,5-difluoro-1,4-dinitrobenzenes;
reacting 2,5-difluoro-1,4-dinitrobenzenes with a first amine or a first alcohol or a first thiol to form a mono-substituted product;
reacting the mono-substituted product with a second amine or a second alcohol or a second thiol, respectively, to form 2,5-disubstituted-1,4-dinitrobenzenes; and
reducing the 2,5-disubstituted-1,4-dinitrobenzenes to form the 2,5-disubstituted-1,4-diaminobenzenes.

6. The process of claim 5, wherein the first amine and the second amine are the same or different, wherein the first alcohol and the second alcohol are the same or different, and wherein the first thiol and the second thiol are the same or different.

7. The process of claim 6, wherein the first amine and the second amine are each selected from the group consisting of primary amines and secondary amines.

8. The process of claim 5, wherein the process of providing 2,5-difluoro-1,4-dinitrobenzenes includes:
reacting 2,5-difluoroanilines with acetic anhydride to form N-(2,5-difluorophenyl)acetamides;
nitrating the N-(2,5-difluorophenyl)acetamides to form N-(2,5-difluoro-4-nitrophenyl)acetamides;
deprotecting the N-(2,5-difluoro-4-nitrophenyl)acetamides to form 2,5-difluoro-4-nitroaniline having an amino group in the 1 position; and
oxidizing the amino group to the corresponding nitro group to form the 5-difluoro-1,4-dinitrobenenes.

9. The process of claim 5 wherein the 2,5-disubstituted-1,4-diaminobenzenes have the general formula

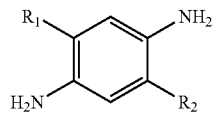

where $R_1$ and $R_2$ are the different and $R_1$ and $R_2$ are each selected from the group consisting of $R_3NH-$, $R_4R_5N-$, $R_6O-$, and $R_7S-$, where $R_3$, $R_4$, $R_5$, $R_6$, and $R_7$ are each independently selected from the group consisting of substituted and unsubstituted hydrocarbon groups containing from 1 to 24 carbon atoms, branched aliphatic groups, linear lower aliphatic groups, cyclic aliphatic groups, homocyclic aryl groups, and heterocyclic aryl groups.

10. The composition of claim 4, wherein $R_1$ and $R_2$ are each selected from the group consisting of $R_3NH-$, $R_6O-$, and $R_7S-$, where $R_3$, $R_6$, and $R_7$ are each independently selected from the group consisting of substituted and unsubstituted hydrocarbon groups containing from 1 to 24 carbon atoms, branched aliphatic groups, linear lower aliphatic groups, cyclic aliphatic groups, and heterocyclic aryl groups.

11. The composition of claim 1 wherein the composition is prepared by:

providing 2,5-difluoro-1,4-dinitrobenzenes;
reacting 2,5-difluoro-1,4-dinitrobenzenes with a first amine to form mono-substituted products;
reacting the mono-substituted product with a second amine to form 2,5-disubstituted-1,4-dinitrobenzenes; and
reducing the 2,5-disubstituted-1,4-dinitrobenzenes to form the 2,5-disubstituted-1,4-diaminobenzenes.

12. The composition of claim 11, wherein the asymmetrical 2,5-disubstituted-1,4-diaminobenzene has the general formula

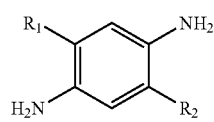

where $R_1$ and $R_2$ are different, and wherein $R_1$ and $R_2$ are each selected from the group consisting of $R_3NH-$ and $R_4R_5N-$, where $R_3$, $R_4$, and $R_5$ are each independently selected from the group consisting of substituted and unsubstituted hydrocarbon groups containing from 1 to 24 carbon atoms, branched aliphatic groups, linear lower aliphatic groups, cyclic aliphatic groups, homocyclic aryl groups, and heterocyclic aryl groups.

* * * * *